United States Patent [19]

Johnson

[11] 4,404,066
[45] * Sep. 13, 1983

[54] METHOD FOR QUANTITATIVELY DETERMINING A PARTICULAR SUBSTRATE CATALYZED BY A MULTISUBSTRATE ENZYME

[75] Inventor: Jay M. Johnson, Dayton, Ohio

[73] Assignee: The Yellow Springs Instrument Company, Yellow Springs, Ohio

[ * ] Notice: The portion of the term of this patent subsequent to Oct. 26, 1999, has been disclaimed.

[21] Appl. No.: 377,765

[22] Filed: May 13, 1982

Related U.S. Application Data

[63] Continuation-in-part of Ser. No. 181,459, Aug. 25, 1980, Pat. No. 4,356,074.

[51] Int. Cl.³ .................... G01N 27/54; C12N 9/04
[52] U.S. Cl. .................... 204/1 T; 204/403; 435/190; 435/817
[58] Field of Search ......... 204/1 E, 195 B, 195 P, 204/403; 435/190, 817

[56] References Cited

U.S. PATENT DOCUMENTS

| | | | |
|---|---|---|---|
| 3,919,052 | 11/1975 | Fresnel et al. | 435/817 X |
| 4,016,044 | 4/1977 | Fresnel et al. | 435/817 X |
| 4,073,713 | 2/1978 | Newman | 204/195 B |
| 4,129,478 | 12/1978 | Racine et al. | 204/1 T |
| 4,220,503 | 9/1980 | Johnson | 204/1 T |
| 4,224,125 | 9/1980 | Nakamura et al. | 204/195 B |

OTHER PUBLICATIONS

G. A. Hamilton et al., "Oxidase and Related Redox Systems", 103, (1965).
Paul J. Taylor et al., Anal. Chem., vol. 49, No. 6, pp. 789–794, (1977).

Primary Examiner—G. L. Kaplan
Attorney, Agent, or Firm—Biebel, French & Nauman

[57] ABSTRACT

A method for control of relative enzyme activity for analytical purposes. The activity of a multisubstrate enzyme may be controlled as a function of the electrical potential applied to the enzyme. The enzyme is preferably incorporated into a thin layer electrochemical cell laminate having exterior membrane layers and an interior enzyme layer. A control electrode located within the enzyme layer applies an electrical potential to the enzyme. An intermediate electron transfer agent may be used to transfer electrons to and from the enzyme and the control electrode.

9 Claims, 7 Drawing Figures

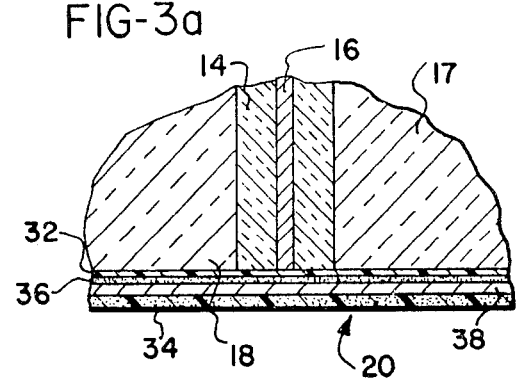
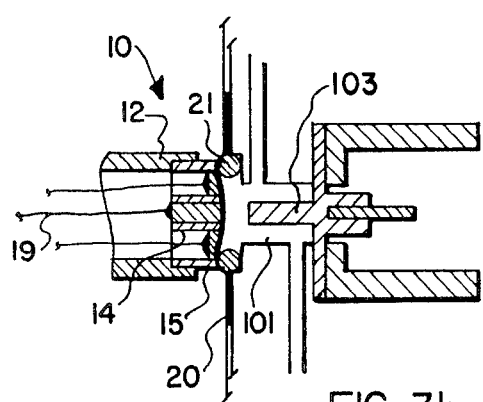
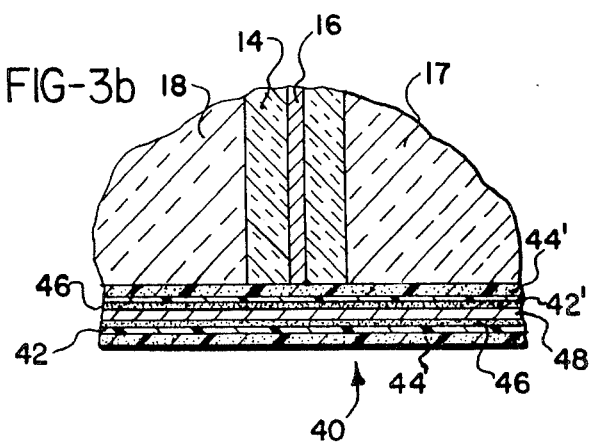
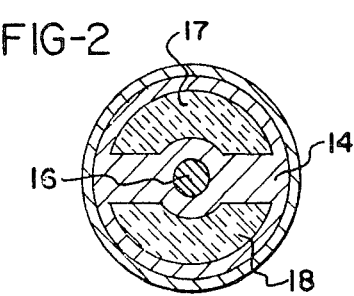

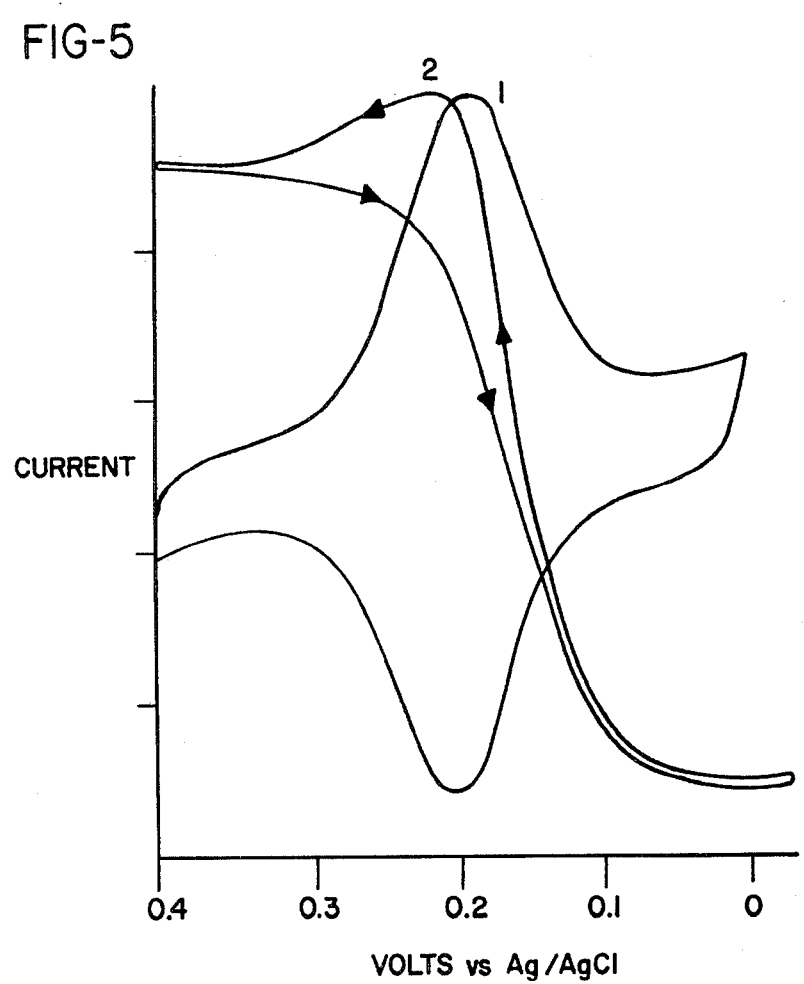

METHOD FOR QUANTITATIVELY DETERMINING A PARTICULAR SUBSTRATE CATALYZED BY A MULTISUBSTRATE ENZYME

CROSS-REFERENCE TO RELATED APPLICATIONS

This application is a continuation-in-part of application Ser. No. 181,459, filed Aug. 25, 1980, now U.S. Pat. No. 4,356,074.

BACKGROUND OF THE INVENTION

This invention relates to enzyme electrodes; in particular it relates to a method for controlling the enzyme activity in an enzyme electrode useful for analytical purposes, and more particularly it relates to a method for controlling substrate specific multisubstrate enzymes utilizing a thin-layer electrochemical cell to control the activity of the enzyme.

Polarographic cell systems have become quite popular in recent years for measurement of various substances. In addition, enzymes have been used in polarographic cells, especially in instances where the unknown substance to be measured is not itself polarographically active, but a material produced or consumed by an enzymatic reaction with that unknown is detectable. For example, it is known that galactose is not polarographically active but that the following reaction takes place in the presence of the enzyme galactose oxidase:

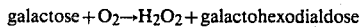

galactose + $O_2 \rightarrow H_2O_2$ + galactohexodialdose

The hydrogen peroxide produced by the reaction can be measured in a polarographic cell such as the system taught by Clark, U.S. Pat. No. 3,539,455. Since the hydrogen peroxide produced is in direct proportion to the amount of galactose present, it is theoretically possible to quatitatively determine the amount of glactose present in a sample where this is unknown. Likewise, it is possible to quantitatively determine the amount of galactose present by measuring the amount of oxygen used in the above reaction mechanism.

Unfortunately, the enzyme galactose oxidase is a nonspecific enzyme which catalyzes the production of hydrogen peroxide and oxygen consumption from a variety of substrates including galactose, glycerin, dihydroxyacetone, and glyceraldehyde. The term "substrate" is understood to include a distinct chemical entity or a class of chemical entities. In many instances, two or more of these compounds will be present together. For example, galactose and glycerin are both found in blood plasma. Present polarographic measuring systems using galactose oxidase are incapable of distinguishing between these compounds because of the nonspecificity of galactose oxidase. This is also true of other multisubstrate enzymes. Accordingly, the need exists in the art for a method of controlling the relative substrate preference of multisubstrate enzymes in order to enable determinative polarographic measurements to be made.

It is known that certain enzymes and other proteins show an activity dependence based upon the reduction-oxidation (redox) potentials of solutions containing such enzymes. For example, Santhanam et al, 99 *J. American Chemical Society*, 274 (1977), reported that the enzyme urease when adsorbed onto the surface of a mercury coated thermistor, reversibly lost activity (as measured by a temperature change of the thermistor) at a given reducing potential. However, this technique has only limited utility for those proteins which will adsorb directly onto mercury, has a slow response time, and is not very sensitive.

Hamilton et al, 1 *Oxidases and Related Redox Systems*, 103 (1965), in theory teach "control" of the potential of a solution which also contained the enzyme glactose oxidase. Hamilton and his coworkers used a given ratio of ferricyanide to ferrocyanide to chemically control the solution potential. Then, by adding galactose and monitoring the uptake of oxygen with a Clark oxygen electrode to determine activity, they plotted the activity dependence on the solution potential (ratio of ferri-to-ferrocyanide). This approach was time consuming since several solutions had to be made up but, also another problem with it was the uncertainty in the true solution potential seen by the enzyme. This results from the fact that the ratio of ferricyanide to ferrocyanide is not controlled after these compounds are added to the solution and obviously this ratio can change both before and/or during the determination of activity.

Finally, Heineman et al, 47 *Anal. Chem.* 79 (1975), calculated the formal oxidation-reduction potentials ($E°'$) for several enzymes using a thin layer electrochemical cell. By applying a series of differing potentials to a solution containing the enzyme of interest, the ratio of oxidized to reduced components was measured spectrophotometrically and used to plot a linear graph, the intercept of which yielded a formal redox potential value ($E°'$).

Likewise, Caja in "Thin-Layer Cell for Routine Applications," 61 *Analytical Chemistry*, 1328 (July 1979), describes a thin layer cell and a wire thin layer electrode. The thin layer electrode was surrounded by Nafion cation exchange tubing. These workers stressed the permselectivity of the cation exchange membrane and the resulting benefit that only small amounts of solutions containing electroactive anions and/or electroactive large neutral species were required for electrochemical studies. No provisions were made for the introduction of substrates under controlled conditions into the thin layer cell. Also, the configuration described would preclude the rapid determination of enzymatic activity due to the slow equilibration of substrate across the thick Nafion membrane.

Thus, to my knowledge no one has utilized the control of redox potential of a solution containing a multisubstrate enzyme to advantage in a polarographic system.

Control of enzyme reaction rates in areas other than polarography has been suggested. Fresnel in U.S. Pat. Nos. 4,016,044 and 3,919,052 does so in the field of manufacture and treatment of food products by enzyme catalysis. Fresnel teaches that regulation of the enzymatic reactions is achieved by applying a potential to an enzymatic electrode (an enzyme fixed on a solid electronically conductive support) and controlling the value of the potential during the reaction so as to compensate for variations in the reaction conditions and the enzyme activity and thereby ensure a constant reaction rate. The system described by Fresnel in the examples in his patents actually performs a maintenance function in the so-called "regulation" of enzymatic activity. The mechanism by which this maintenance of activity is obtained is indirect, evidently by control of environmental factors such as pH, dielectric, etc. which, in turn, can affect enzyme activity. In the '052 patent Fresnel even suggests that the technique "may allow the specificity of—[the] enzyme to be modified, if need be." However, there is nothing disclosed in this patent concerning specificity beyond that broad suggestion.

Accordingly, the need still remains for a method of directly controlling the relative activity of an enzyme, for example controlling the substrate preference of a non-specific enzyme such as galactose oxidase, in order to enable rapid determinative analytical measurements to be made.

SUMMARY OF THE INVENTION

In accordance with the present invention, the relative activity of the enzyme found in an enzyme electrode is controlled as a function of a redox potential applied to the enzyme. Any multisubstrate enzyme having a redox potential resulting in a direct activity-dependence upon potential may be controlled by use of the present invention. Examples include galactose oxidase, ascorbate oxidase, and xanthine oxidase.

Taking galactose oxidase as illustrative, it is believed that the redox potential control is effective because of the presence of copper ion. Galactose oxidase contains a single copper ion. The enzyme is inactive in the reduced state, $Cu^{+1}$, and active in the oxidized state, $Cu^{+2}$ or $Cu^{+3}$. Whatever the reduction/oxidation mechanism, it is possible with this invention to control enzymatic activity electrochemically. Thus, the activity of the enzyme may be controlled as a function of the electrical potential applied to the enzyme. In this instance, diffusion limiting conditions are required in order to use the enzyme electrode analytically to do quantitative measurements on a solution which contains more than one substrate. This is because the true solution potential dependency of galactose oxidase activity is independent of the substrate used and only under diffusion limiting conditions does the apparent dependence of activity upon solution potential differ for the different substrates. By diffusion limiting conditions, it is meant that high enzyme concentrations are used in a thin layer cell so that diffusion of substrate into the enzyme thin layer is rate limiting. With other enzymes such diffusion limiting conditions are not required; although, placement of the enzyme in a thin layer electrochemical cell is the preferred approach.

The thin layer cell is a laminate having a permeable, outer membrane to separate the analytical electrode from the external bulk solution containing the sample to be analyzed. The thin layer cell itself is less than 10 microns thick and contains the entrapped enzyme which can either be free or immobilized. The control electrode may be either a thin grid of electrically conductive material in the thin layer cell or a layer of electrically conductive material sputtered or otherwise deposited on the back side of the permeable membrane separating the bulk solution and enzyme in the thin layer cell.

The back wall of the thin layer cell can be either an impermeable support material or a permeable or semipermeable membrane. Intermediate electron transfer agents (mediators) are preferrably present in the thin layer cell for transferring electrons between the enzyme and electrode. The mediators enable rapid achievement of solution potential control in the thin layer cell.

The permeability of the outer membrane separating the thin layer cell from the bulk solution is such that the enzyme cannot pass outwardly through the membrane yet substrates of interest can diffuse into the interior of the thin layer cell. The pore size of the outer membrane is also small enough that electrochemical mediating agents are essentially entrapped within the thin layer cell.

In an alternative embodiment, however, the pores may be large enough to permit rapid diffusion of mediators into and out of the thin layer cell, but cross-linking of the enzyme is therefore desirable. In this embodiment the thin layer cell is not "seen" by the mediator as an electrochemical "thin layer" because the mediator can move freely into and out of the thin layer cell through the membrane. However, because the cell containing the enzyme and electrode is to thin, mediated potential control of the enzymatic redox state can still be maintained. One of the advantages of using this embodiment is that substrates of interest which are larger (over 200 molecular weight) can still diffuse into the thin layer cell. This would not be possible if the mediator had to be completely contained within the thin layer.

In operation, the thin layer cell may be coupled to a polarographic cell having an $H_2O_2$ analytical electrode or to a polarographic cell having an oxygen analytical electrode. The separate, control electrode within the thin layer cell is coupled to a source capable of providing varying electrical potential. By measuring the steady state hydrogen peroxide production with the analytical electrode behind the membrane assembly, the relative steady state activity of an oxidase enzyme in the thin layer cell can be determined in the presence of a substrate which is introduced into the bulk solution and allowed to equilibrate across the outer membrane. This technique, therefore, allows the simultaneous control of the solution potential within the thin layer cell and measurement of relative enzymatic activity of the trapped enzyme. The sensitivity of the analytical electrode to $H_2O_2$ is unaffected by changing the solution potential in the eyzyme thin layer. Total consumption by the control electrode of the electroactive product or substrate to be measured should be avoided since this will affect the analytical determination. Anything less than total consumption will not effect that determination.

In analytical use, after standardization, a sample containing one or more substrates of interest is brought into contact with the cell. The activity of the enzyme is controlled by applying an appropriate potential or varying potentials to the control electrode with the thin layer cell. By polarographically measuring the relative amounts of hydrogen peroxide produced at each potential or the oxygen uptake (depending on the type of cell used), it is possible to identify the specific substrate or substrates in the sample; although, the prefered major use is in terms of quantitative determination. Thus, a single potential corresponding to a maximum enzymatic activity level for a specific substrate can be applied to the control electrode within the thin layer cell and the enzyme in the thin layer will be used to produce $H_2O_2$, the determination for which will quantitatively measure the specific substrate of interest.

If there are n(where n is greater than 1) substrates present and the activity potential dependence is not different enough, then a measurement at each of n potential (for maximum relative difference) is required for accurate quantitative determination.

Accordingly, it is an object of the present invention to provide a process for directly controlling the relative activity of an enzyme in an enzyme electrode in order to enable rapid determinative analytical measurements to be made. This and other objects and advantages of the invention will be apparent from the following description, the accompanying drawings, and the appended claims.

BRIEF DESCRIPTION OF THE DRAWINGS

FIG. 1 is a schematic view of a polarographic cell having in place the thin layer electrochemical cell of the present invention;

FIG. 2 is a front view of the face of the electrode arrangement found in FIG. 1.

FIG. 3 is an enlarged view of the lower central portion of the polarographic cell of FIG. 1 and showing in more detail one embodiment of the thin layer electrochemical cell of the present invention; and FIG. 3b is an enlarged view of the lower central portion of the polarographic cell of FIG. 1 and showing in detail a second embodiment of the thin layer electrochemical cell.

FIG. 5 is an activity potential profile for the galactose oxidase catalyzed oxidation of dihydroxyacetone, showing both the current-potential curve for the oxidation/reduction of ferrocyanide/ferricyanide (1) and a plot of the hydrogen peroxide current (2) resulting from the enzyme reaction.

DESCRIPTION OF THE PREFERRED EMBODIMENTS

Figure 4A:
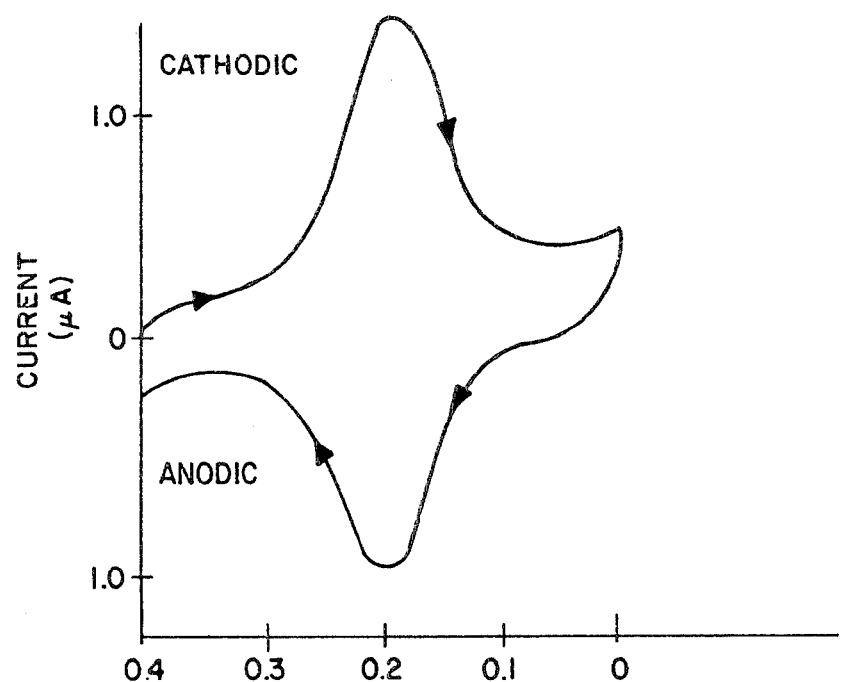
FIG. 4a is the current-potential curve for the oxidation/reduction of ferrocyanide/ferricyanide at the electrode in the thin layer.

Referring to FIG. 1, there is shown a thin layer electrochemical cell of the present invention in combination with a polarographic cell system. The polarographic cell assembly 10 includes an insulating support body 12 of plastic or glass which is preferably cylindrical in shape. Positioned within the cylindrical support body 12 is an electrically insulating member 14 of plastic or glass which supports an analytical electrode such as platinum anode 16 and two silver/silver chloride reference electrodes 17 and 18 (see FIG. 2). A conductor 19 is attached to analytical anode 16.

The lower end of support body 12 is provided with an annular ring or retainer 15, and a thin layer electrochemical cell 20 made in accordance with the present invention is maintained on the end of the support body 12 nearest electrodes 16, 17 and 18. The thin layer cell is held in position on the support body by an O-ring 21 or the like.

In the embodiment illustrated in FIG. 3a, thin layer cell 20 has as a back wall an inner membrane layer 32 against the face of analytical anode 16 and reference electrodes 17 and 18. Outer membrane layer 34 will be in contact with the sample to be analyzed. On the back side of outer membrane layer 34, a control electrode in the form of electrically conductive layer 38 such as gold is deposited by a sputtering or other known process. Electrically conductive layer 38 is used to apply an electrical potential to the enzyme in enzyme layer 36 which in turn varies the activity of the enzyme, thereby controlling the relative substrate preference of the enzyme. The enzyme may be immobilized in enzyme layer 36 by the addition of binders or cross-linking agents such as glutaraldehyde. A preferred method of forming enzyme layer 36 is to mix the enzyme and binder or cross-linking agent with enough liquid to form a flowable paste which can then be pressed into a thin, uniform layer. Sufficient enzyme must be incorporated into the mixture to provide an adequate reactive amount for measurement.

In the embodiment illustrated in FIG. 3b thin layer cell 40 comprises a pair of coupled membrane layers, outer one 42–44 and inner one 42′–44′ sandwiching an enzyme layer 46 which contains a control electrode 48 in the form of an electrically conductive layer running therethrough. Control electrode 48 may comprise a grid of fine gold wire or other electrically conductive material. In this embodiment, the enzyme does not need to be immobilized since the pore size of the membrane layers 42 and 42′ is such that the enzyme is too large to pass through.

In both embodiments 3a and 3b, membrane layers 32 and 42, 42° comprises a thin film of essentially homogenous silicone, polymethyl methacrylate, or cellulose acetate. In a preferred embodiment, layers 32 and 42, 42′ are an approximately 0.10–1.0 micron thick layer of cellulose acetate having a pore size of 6 A° in diameter. Membrane layers 34 and 44, 44′ are preferably a 5–10 micron thick polycarbonate film. The pores size may vary. In embodiment 2a membrane 34 has a pore size preferrably around 0.03 micron and the pore density of preferrably $3 \times 10^8$ pores/cm$^2$. In embodiment 2b the membrane layers 44, 44′ are simply gross support layers which may have a pore size of around 12 microns in diameter and a pore density of $1 \times 10^5$ pores/cm$^2$. Membrane layers 44, 44′ of FIG. 2b are used as a support for the thinner membrane layers 42, 42′ and also acts as a gross filter to screen out very large interfering compounds from the bulk solution to be sampled. A more detailed description of the methods of preparing laminates of membrane layers of this type as well as the preparation of the enzyme layer is found in Newman, U.S. Pat. No. 3,979,274, the disclosure of which is hereby incorporated by reference.

Because of the thinness of the layers, thin layer cell 20 or 40 permits rapid diffusion of the substrate of interest into the cell and exhibits an extremely rapid response time with steady state being reached in less than one minute. In the embodiment shown in FIG. 2a, inner membrane layer 32 is preferably 0.1–1 micron thick, and outer membrane layer 34 is 5–10 microns thick, enzyme layer 36 is around 0.1–2 microns thick, and the electrically conductive layer 38 may be extremely thin so long as the resistance is less than around 1000 ohms/cm$^2$. The embodiment shown in FIG. 2b is only somewhat thicker with membrane layers 42,42′ preferably again being 0.1–1 micron thick, membrane layers 44, 44′ are 5–10 microns thick, and the overall thickness of the enzyme layer 46 and control electrode 48 being about 3–10 microns thick, with the control electrode 48 around 1–5 microns.

Referring again to FIG. 1, in operation cell assembly 10 with thin layer cell 20 of the type shown in FIG. 3a, for example, in position is in contact with a sample solution injected into chamber 101 which is stirred by stirring finger 103. In a matter of seconds, oxygen and the substrate of interest will diffuse into the thin layer cell through outer membrane layer 34 and react with the galactose oxidase enzyme in enzyme layer 36. This reaction produces hydrogen peroxide which diffuses through inner membrane layer 32 to contact the active surface of the platinum analytical anode 16. An ammeter (not shown) then measures the amount of hydrogen peroxide produced as a measure of the concentration of the substrate in the sample solution. Because of the extreme thinness of cell 20, there is a delay from the time of hydrogen peroxide production to detection at anode 16 of only a few seconds. A silver/silver chloride electrode 17 acts as a reference electrode and completes the hydrogen peroxide detection circuit.

In cases where there are two or more substrates in the sample solution which will react with the enzyme the solution potential of the enzyme for a given substrate is controlled under diffusion limiting conditions as required in some instances, by controlling the electrical potential of electrically conductive layer 38 in the thin layer cell 20 which in turn controls the oxidation state of the enzyme in enzyme layer 36 and renders it relatively specific toward a selected substrate. In a preferred embodiment of the invention, an intermediate electron transfer agent (mediator) is present in the enzyme layer 36 and acts to transfer electrons from the electrically conductive layer to the enzyme. An example of such a mediator is potassium ferricyanide which is capable of reversibly exchanging electrons with the electrically conductive layer and enzyme as it is alternately reduced to the ferrocyanide state and reoxidized to ferricyanide. Other suitable mediators may be used such as Co (terpyridine)$_2$Cl$_2$, K$_4$W(CN)$_8$, or 2,6 dichlorophenolindophenol.

In the thin layer cell 40 illustrated in FIG. 3b, the permeability of the coupled inner membrane layers 42'-44' and coupled outer membrane layer 42-44, is such that the enzyme and mediator are essentially entrapped within the cell. However, in the thin layer cell illustrated in FIG. 3a, the pore sizes in outer membrane layer 34 are large enough to permit the rapid passage of mediators into and out of cell 20. In this case, the thin layer cell 20 is no longer a "thin layer" in the electrochemical sense to the mediator since it is free to diffuse into and out of the cell. Yet, mediated potential control of the oxidation and reduction states of enzyme can be maintained because of the thinness of the membrane layers. This is an advantage in cases where a substrate of interest is large and could not be introduced into the thin layer cell if it were necessary to completely contain the mediator in the cell.

Electrical potentials are applied to electrically conductive layer 38 (FIG. 3a) and control electrode 48 (FIG. 3b) by a potentiostat of conventional operational amplifier design. A silver/silver chloride electrode 18 acts as a reference electrode for the potential control circuit while a platinum electrode (not shown) may be placed in the sample solution to act as an auxiliary electrode.

The invention may be better understood by reference to the following nonlimiting examples.

EXAMPLE 1

A thin layer cell as shown in FIG. 3b was constructed using a gold grid control electrode and galactose oxidase as the enzyme. A scanning rate of 2 millivolts/second was used. The substrate tested for was glycerin. The enzyme layer contained buffered $4 \times 10^{-3}$ molar potassium ferricyanide as a mediator. The sample solution had a pH of 7.3 and also contained $4 \times 10^{-3}$ molar potassium ferricyanide in 0.5 molar potassium chloride with a 0.07 molar phosphate buffer. As shown by the cyclic voltammogram in FIG. 4A, which is a current-potential curve for the oxidation/reduction of ferrocyanide/ferricyanide ion at the gold grid, as the potential of the gold grid is scanned from 0 volt versus Ag/AgCl to 0.4 volt, the anodic current peak indicates the oxidation of ferrocyanide ion to ferricyanide. A reversal of the scan results in a cathodic peak due to the reduction back to ferrocyanide. Since the mediator is trapped within the cell, the voltammogram exhibits a typical thin layer behavior with negligible peak separation and peak widths at a half-height of approximately 90 millivolts.

Figure 4B:
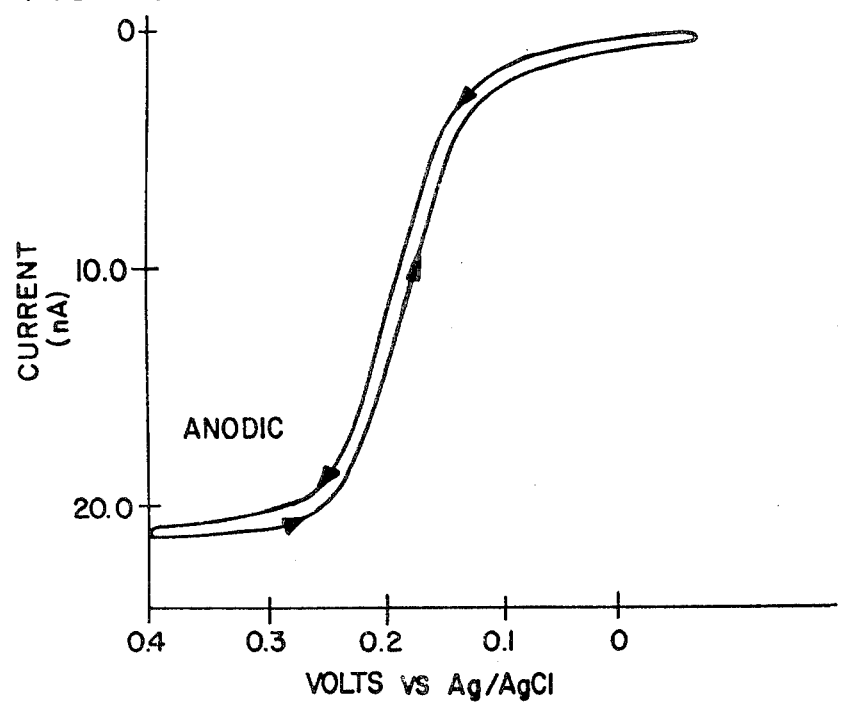
FIG. 4b is an activity potential profile for the galactose oxidase catalyzed oxidation of glycerin having a plot of the hydrogen peroxide current resulting from the enzyme reaction.

A positive potential scan converts the galactose oxidase into its oxidized form which catalyzes the substrate's reaction with oxygen. The reaction produces hydrogen peroxide which is detected by the platinum analytical electrode. FIG. 4B is a plot of the hydrogen peroxide current measured amperometrically as the gold grid electrode was scanned at 2 millivolts/second. Scanning began after the glycerin substrate was introduced into the stirred sample solution until a final concentration of about $5 \times 10^{-3}$ molar and a steady state hydrogen peroxide current had been achieved. The onset of a limiting current at about 0.3 volt versus Ag/AgCl is indicative of complete galactose oxidase conversion to its oxidized form. The approximate reversibility of the oxidation/reduction reaction is indicated by the reverse scan behavior shown in FIG. 4B.

The voltammogram of FIG. 4B is a unique measurement of enzyme activity as a function of solution potential. The shape of the wave is determined by several factors including diffusion of the substrate from the sample solution into the thin layer, the fraction of galactose oxidase which is in the enzymatically active oxidation state, the kinetics of the substrate enzyme reaction, and subsequent diffusion of hydrogen peroxide to the platinum electrode. Results utilizing other substrates indicate that the wave shape will differ for different substrates.

For example, FIG. 5 shows a plot of the hydrogen peroxide current measured amperometrically as a function of the potential of the gold grid when a dihydroxyacetone substrate was introduced into a sample solution at a final concentration of about $3 \times 10^{-4}$ molar. Superimposed over it is the current-potential curve for the oxidation/reduction of ferrocyanide/ferricyanide similar to that depicted in FIG. 4A. A comparison of FIGS. 4A, 4B and 5 shows that by controlling the potential of the gold grid, and with it the oxidation state of galactose oxidase, the relative specificity of the enzyme for various substrates can be controlled. By measuring the relative amounts of hydrogen peroxide produced as the potential of the gold grid is changed, the specific substrates which react with galactose oxidase may be identified and their relative concentrations determined by polarographic measurement.

EXAMPLE II

A thin layer cell as in FIG. 3A was used for measurements performed on aqueous solutions containing various concentrations of a single substrate as follows: (1) the appropriate potential was set on the gold control electrode, (2) 25 ml of the substrate solution to be measured was injected into the sample chamber, (3) after a steady state H$_2$O$_2$ current was achieved (0.5-1 min. depending on the substrate), the H$_2$O$_2$ current was recorded and (4) the sample chamber was cleared and the background current allowed to reach a constant low level before this procedure was repeated on the next solution.

In all cases, a solution which was near the middle of the range in concentration was used as a standard and the other solutions treated as "unknowns". The solution used as a standard was injected before and after the solutions treated as "unknowns". The currents obtained for the standard before and after injection of a given "unknown" were averaged and this average value used to calculate the concentration of the particular substrate in the "unknown".

involving concentration are presented in terms of the concentration of substrate injected into the instrument. The final concentration of substrate in the bulk solution is about one seventh of the concentration injected. Time to 99% of steady state (S.S.) is calculated by setting the response obtained at one minute after injection of any given substrate equal to 100% and then determining the time from injection at which the response equals 99% of the response at one minute. The upper limit of the linear range shown is only approximate since to some degree it will depend upon the absolute sensitivity of any given

TABLE I

| Substrate (M.W.) | ~Apparent Half-Wave Potential (mV vs SCE) | ~Set Potential (mV vs SCE) | Avg. Relative Sensitivity | Time to 99% S.S. (sec.) | Lower Detection Limit (mM) | ~Upper Limit of Linear Range (mM) | Linear Regression Intercept (mM)/Slope | Pooled Estimate S.D. (mM) |
|---|---|---|---|---|---|---|---|---|
| Glycerin | +170 | +290 | 0.38 | 45 | 0.04 | 40 | −0.213/1.038 | ±0.19 |
| (92.09) | | +90 | 0.04 | | 0.4 | 400 | −3.251/1.024 | ±2.87 |
| Glyceraldehyde | +140 | +290 | 0.39 | 47 | 0.04 | 40 | −1.350/1.110 | ±0.78 |
| (90.08) | | +60 | 0.04 | | 0.4 | 400 | −2.461/1.018 | ±7.68 |
| Lactose | +120 | +290 | 0.56 | 32 | 0.03 | 25 | +0.007/1.002 | ±0.11 |
| (342.30) | | +60 | 0.11 | | 0.2 | 150 | −0.951/1.028 | ±0.80 |
| Galactose | +80 | +290 | 1.00 | 16 | 0.02 | 15 | −0.003/1.010 | ±0.12 |
| (180.16) | | +30 | 0.25 | | 0.1 | 70 | −0.081/1.008 | ±0.75 |
| Dihydroxyacetone | +70 | +290 | 3.33 | 26 | 0.005 | 6 | +0.037/1.027 | ±0.10 |
| (90.08) | | +30 | 0.80 | | 0.03 | 20 | −0.220/1.027 | ±0.77 |
| Stachyose | +60 | +290 | 0.86 | 19 | 0.02 | 15 | −0.001/1.016 | ±0.05 |
| (666.64) | | +10 | 0.22 | | 0.1 | 70 | +0.086/1.007 | ±0.53 |
| Raffinose | +60 | +290 | 0.92 | 21 | 0.02 | 15 | −0.042/1.020 | ±0.07 |
| (504.46) | | +10 | 0.23 | | 0.1 | 70 | −1.028/1.052 | ±1.18 |

The use of internal solution potential control (via a control electrode) to maintain solution potential at a high level (+0.3 V vs SCE) in this enzyme-electrode renders the electrode more sensitive over time (days) to the poorer substrates by as much as a factor of 1.5 to 2 times what it is if the mediator-titrant alone is used to chemically "control" the solution potential in the enzyme-layer. The major reaction for this appears to be the fact that without the control electrode the solution potential of a mediator-titrant solution (ferricyanide, for example) made up with the oxidized form can over time slowly drift toward the midpoint potential of the mediator-titrant couple and thus the activity of the immobilized galactose oxidase will decrease. This phenomenon is quite variable and may be related to either the tendency of reducing solution contaminants to reduce the mediator-titrant or the instability of the mediator-titrant over time. However, as a result, the sensitivity to those substrates which are not diffusion limited drops off accordingly without a control electrode.

Table I illustrates the response characteristics to various substrates obtained at different set potentials. The apparent half-wave potential (+5 mV) for any given substrate was measured and reflects the apparent dependence of enzyme activity upon solution potential for that substrate in this system with no correction for IR drop. This is an apparent half-wave potential since at the enzyme concentration used here (570 I.U./microliter) the dependence of enzyme activity upon solution potential for any given substrate is distorted due to the effects of diffusion. The set potential is the potential set on the gold control membrane electrode. At a set potential of +0.290 V vs SCE the enzyme-electrode has maximal sensitivity to all substrates. Relative sensitivity is expressed relative to galactose sensitivity within a given membrane and then averaged over ten membranes to obtain the average relative sensitivity. (The average absolute sensitivity for galactose was 12.03 n A/mM.) In all cases, sensitivity data and other data membrane. The linear regression equation was calculated with y=the concentration to which the standard was made and x=concentration measured. An ideal fit, therefore, would be represented by a slope of 1.000 and an intercept of zero. Each regression equation was calculated using the average of three determinations (each done on a different membrane) on a total of six standards falling within the linear response range for any given substrate. In every case, the correlation coefficient obtained for the regression equation was at least 0.999. The pooled estimate of the standard deviation was calculated as described in reference (24) and in each case n=18 (3 determinations×6 standards).

As can be seen in Table I, the use of internal solution potential control via the control electrode allows the sensitivity to any given substrate to be controlled and maintained (reversibly) over as much as a factor of ten depending upon how close the set potential on the control electrode is to the apparent half-wave potential for that substrate. Also, as would be expected, in general the errors (accuracy and precision) and the detection limits increase in inverse proportion to the sensitivity. Thus, using this technique the working range of the enzyme-electrode can be rapidly increased by as much as a factor of ten and possibly further simply by changing the control electrode potential. This effectively results in an increase in the dynamic range of the enzyme electrode by as much as a factor of ten.

In this manner an enzyme electrode may be used to determine those substrates for which a multisubstrate enzyme will catalyze the production of hydrogen peroxide. It can do so rapidly and accurately with specificity as to the particular substrate involved. Thus, a direct, reversible, rapid analytical measurement technique is provided.

While the processes herein described constitute preferred embodiments of the invention, it is to be understood that the invention is not limited to this precise process and that changes may be made therein without departing from the scope of the invention.

What is claimed is:

1. In a method for quantitatively determining the amount of a particular substrate, catalyzed by a multisubstrate enzyme (having a direct redox dependent activity) to react with oxygen and form hydrogen peroxide as a reaction product, wherein the improvement comprises the steps of: applying an electrical potential to said enzyme, said electrical potential being sufficient to control the activity of said multisubstrate enzyme, contacting said enzyme with a solution containing at least said particular substrate, and measuring for an electroactive reactant or product of the reaction mechanism whereby a rapid, direct quantitative analysis is obtained.

2. The method of claim 1 wherein a single substrate is present and said electrical potential is maintained at a predetermined level in order to boost and stabilize the activity of the substrate.

3. The method of claim 1 wherein more than one substrate is present and said electrical potential is selected to eliminate activity toward all but one of the substrates.

4. In a method for quantitatively determining the amounts of particular substrates, catalyzed by a multisubstrate enzyme (having a direct redox dependent activity) to react with oxygen and form hydrogen peroxide as a reaction product, wherein the improvement comprises the steps of: applying at least two different electrical potentials to said enzyme, said electrical potentials being sufficient to render different the relative sensitivity of the enzyme for at least two of the substrates present, contacting said enzyme with a solution containing at least two substrates, and measuring for an electroactive reactant or product of the reaction mechanism whereby a rapid, direct quantitative analysis is obtained.

5. The method of claim 4 wherein galactose oxidase is the multisubstrate enzyme and said method is conducted under essentially diffusion limiting conditions.

6. In a method of measuring for the presence of substrates, catalyzed by a multisubstrate enzyme (having a direct redox dependent activity) to react with oxygen and form hydrogen peroxide as a reaction product, wherein the improvement comprises the steps of: applying an electrical potential to said enzyme, contacting said enzyme with a solution containing at least one substrate catalyzed by said enzyme, continuously varying the electrical potential applied and measuring for an electroactive reactant or product of the reaction mechanism as a function of the potential applied to said enzyme whereby a rapid, direct qualitative analysis is obtained.

7. The method of claim 1, 4 or 6 wherein hydrogen peroxide is the electroactive product being measured.

8. The method of claim 1 or 6 wherein galactose oxidase is the multisubstrate enzyme.

9. The method of claims 1, 4 or 6 wherein said multisubstrate enzyme is positioned between a first outer membrane layer and a second inner membrane layer, said first outer membrane layer adapted to be adjacent said solution and allowing passage of low molecular weight materials therethrough but excluding high molecular weight materials contained in said solution, said second inner membrane layer adapted to be adjacent the means for measuring said electroactive reactant or product of the reaction mechanism and excluding passage of interfering low molecular weight materials and any mediator but permitting passage of said electroactive reactant or product of the reaction mechanism, and said electrical potential is applied to said enzyme by an electrically conductive layer positioned between said first and second membrane layers and in contact with said enzyme.

* * * * *